(12) United States Patent
Locke et al.

(10) Patent No.: US 11,771,599 B2
(45) Date of Patent: Oct. 3, 2023

(54) EXTENDED WEAR-TIME DRESSING

(71) Applicant: KCI Licensing, Inc., San Antonio, TX (US)

(72) Inventors: Christopher Brian Locke, Bournemouth (GB); Kristine M. Kieswetter, San Antonio, TX (US); Timothy Mark Robinson, Shillingstone (GB)

(73) Assignee: KCI Licensing, Inc., San Antonio, TX (US)

( * ) Notice: Subject to any disclaimer, the term of this patent is extended or adjusted under 35 U.S.C. 154(b) by 511 days.

(21) Appl. No.: 16/759,935

(22) PCT Filed: Oct. 22, 2018

(86) PCT No.: PCT/US2018/056914
§ 371 (c)(1),
(2) Date: Apr. 28, 2020

(87) PCT Pub. No.: WO2019/089266
PCT Pub. Date: May 9, 2019

(65) Prior Publication Data
US 2020/0323692 A1 Oct. 15, 2020

Related U.S. Application Data

(60) Provisional application No. 62/581,540, filed on Nov. 3, 2017.

(51) Int. Cl.
*A61F 13/00* (2006.01)
*A61L 15/22* (2006.01)
(Continued)

(52) U.S. Cl.
CPC .. *A61F 13/00068* (2013.01); *A61F 13/00012* (2013.01); *A61L 15/225* (2013.01);
(Continued)

(58) Field of Classification Search
None
See application file for complete search history.

(56) References Cited

U.S. PATENT DOCUMENTS

| 1,355,846 A | 10/1920 | Rannells |
| 2,547,758 A | 4/1951 | Keeling |

(Continued)

FOREIGN PATENT DOCUMENTS

| AU | 550575 B2 | 3/1986 |
| AU | 745271 B2 | 3/2002 |

(Continued)

OTHER PUBLICATIONS

Cullen et al. "The role of oxidized regenerated cellulose/collagen in chronic wound repairand its potential mechanism of action", International Journal of Biochemistry & Cell Biology, 34(2002), 1544-1556 (Year: 2002).*

(Continued)

*Primary Examiner* — Isis A Ghali

(57) ABSTRACT

As an example, in some embodiments is a dressing that may comprise a manifold, a bioresorbable component, and a degradation-modulating component. The degradation-modulating component may cover two or more surfaces of the bioresorbable component. The degradation-modulating component may be further configured to modulate degradation of the bioresorbable component.

5 Claims, 3 Drawing Sheets

(51) Int. Cl.
  *A61L 15/26* (2006.01)
  *A61L 15/42* (2006.01)
  *A61L 15/44* (2006.01)
  *A61L 15/62* (2006.01)
  *A61L 15/64* (2006.01)
  *A61M 1/00* (2006.01)

(52) U.S. Cl.
  CPC ............ *A61L 15/26* (2013.01); *A61L 15/425* (2013.01); *A61L 15/44* (2013.01); *A61L 15/62* (2013.01); *A61L 15/64* (2013.01); *A61M 1/90* (2021.05)

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 7,846,141 B2 | 12/2010 | Weston |
| 8,062,273 B2 | 11/2011 | Weston |
| 8,216,198 B2 | 7/2012 | Heagle et al. |
| 8,251,979 B2 | 8/2012 | Malhi |
| 8,257,327 B2 | 9/2012 | Blott et al. |
| 8,398,614 B2 | 3/2013 | Blott et al. |
| 8,449,509 B2 | 5/2013 | Weston |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,679,081 B2 | 3/2014 | Heagle et al. |
| 8,834,451 B2 | 9/2014 | Blott et al. |
| 8,926,592 B2 | 1/2015 | Blott et al. |
| 9,017,302 B2 | 4/2015 | Vitaris et al. |
| 9,198,801 B2 | 12/2015 | Weston |
| 9,211,365 B2 | 12/2015 | Weston |
| 9,289,542 B2 | 3/2016 | Blott et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2008/0208171 A1* | 8/2008 | Argenta ............... A61M 1/90 604/540 |
| 2010/0086578 A1* | 4/2010 | Nielsen ................. A61L 31/005 424/423 |
| 2011/0077604 A1* | 3/2011 | Weston ................. A61M 1/982 604/313 |
| 2011/0091515 A1 | 4/2011 | Zilberman et al. |
| 2011/0251566 A1 | 10/2011 | Zimnitsky et al. |
| 2012/0107366 A1 | 5/2012 | Kapiamba |
| 2014/0163491 A1 | 6/2014 | Schuessler et al. |
| 2015/0080788 A1 | 3/2015 | Blott et al. |
| 2015/0320434 A1 | 11/2015 | Ingram et al. |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |

(56) References Cited

FOREIGN PATENT DOCUMENTS

| | | |
|---|---|---|
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| EP | 2537538 A1 | 12/2012 |
| GB | 692578 A | 6/1953 |
| GB | 2195255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/20041 A1 | 9/1994 |
| WO | 96/05873 A1 | 2/1996 |
| WO | 97/18007 A1 | 5/1997 |
| WO | 99/13793 A1 | 3/1999 |
| WO | 2008/091521 A2 | 7/2008 |
| WO | 2009097534 A1 | 8/2009 |
| WO | 2013078214 A1 | 5/2013 |

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.
Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634 639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & dated Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of ntermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and p. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and ceilified translation).
M. Schein, R. Saadia, J R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.L Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Nournal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract,

(56) References Cited

OTHER PUBLICATIONS editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C.® Therapy Clinical Guidelines: A Reference Source for Clinicians; Jul. 2007.

International Search Report and Written Opinion for Corresponding Application No. PCT/US2018/056914, dated Feb. 4, 2019.

Japanese Notice of Rejection Corresponding to Application No. 2020-524154, dated Sep. 6, 2022.

\* cited by examiner

EXTENDED WEAR-TIME DRESSING

RELATED APPLICATIONS

The present invention claims the benefit, under 35 USC § 119(e), of the filing of U.S. Provisional Patent Application Ser. No. 62/581,540, entitled "Extended Wear-Time Dressing," filed Nov. 3, 2017. This provisional application is incorporated herein by reference for all purposes.

TECHNICAL FIELD

The invention set forth in the appended claims relates generally to treatment of a tissue site and, more particularly, but with limitation, to dressings for application to a tissue site, to systems including such dressings and to methods related to the same.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds or other tissue with reduced pressure may be commonly referred to as "negative-pressure therapy," but is also known by other names, including "negative-pressure wound therapy," "reduced-pressure therapy," "vacuum therapy," "vacuum-assisted closure," and "topical negative pressure," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

While the clinical benefits of negative-pressure therapy are widely known, improvements to therapy systems, components, and processes may benefit healthcare providers and patients.

BRIEF SUMMARY

Systems, apparatuses such as a dressing, and methods for using the same, for example, in a negative-pressure therapy environment, are set forth in the appended claims. Illustrative embodiments are also provided to enable a person skilled in the art to make and use the claimed subject matter.

For example, in some embodiments a dressing having an extended wear-time may include one or more dressing layers or components, and at least one component for modulating the degradation of other components or layers. Such dressings may be suitable for negative-pressure therapy systems in some embodiments.

Some embodiments of a dressing may comprise a manifold, a bioresorbable component, and degradation-modulating component. In some embodiments, the degradation-modulating component may be configured to modulate degradation of at least one of the bioresorbable component. In some embodiments, the bioresorbable component may comprise collagen and oxidized, regenerated cellulose. In some embodiments, the degradation-modulating component may comprise a polymer having one or more monomeric units. In some embodiments the monomeric unit present in the polymer may be derived from another monomeric unit that has been modified, for example, functionalized, after polymerization. The monomeric repeating unit may comprise vinyl pyrrolidone, vinyl alcohol (for example, which may be derived from vinyl acetate), ethylene oxide, propylene oxide, ethylene glycol, acrylic acid, a salt of acrylic acid, an ester of acrylic acid, acrylamido methylpropane sulphonic acid, a salt of acrylamido methylpropane sulphonic acid, an ester of acrylamido methylpropane sulphonic acid, cellulose derivatives, copolymers thereof, blends or mixtures thereof, or combinations thereof. For example, the polymer may comprise polyvinyl pyrrolidone, polyvinyl alcohol, polyethylene glycol, polypropylene glycol, poly (acrylic acid), or poly(acrylamido methylpropane sulphonic acid).

In some embodiments, a system for providing negative-pressure therapy to a tissue site may comprise a dressing. The dressing may comprise a manifold, a bioresorbable component, and a degradation-modulating component. In some embodiments, the degradation-modulating component may be configured to modulate degradation of the bioresorbable component. In some embodiments, the bioresorbable component may comprise collagen and oxidized, regenerated cellulose. In some embodiments, the degradation-modulating component may comprise a polymer having one or more monomeric units. In some embodiments the monomeric unit present in the polymer may be derived from another monomeric unit that has been modified, for example, functionalized, after polymerization. The monomeric unit may comprise vinyl pyrrolidone, vinyl alcohol (for example, which may be derived from vinyl acetate), ethylene oxide, propylene oxide, ethylene glycol, acrylic acid, a salt of acrylic acid, an ester of acrylic acid, acrylamido methylpropane sulphonic acid, a salt of acrylamido methylpropane sulphonic acid, an ester of acrylamido methylpropane sulphonic acid, cellulose derivatives, copolymers thereof, blends or mixtures thereof, or combinations thereof. For example, the polymer may comprise polyvinyl pyrrolidone, polyvinyl alcohol, polyethylene glycol, polypropylene glycol, poly(acrylic acid), or poly(acrylamido methylpropane sulphonic acid). The system may also comprise a negative-pressure source configured to be fluidly coupled to the manifold.

Example embodiments of methods for providing negative-pressure therapy to a tissue site are also described. A method may comprise, for example, positioning dressing including a manifold, a component, and a degradation-modulating component proximate to the tissue site. The dressing may be positioned such that the degradation-modulating component may be configured to modulate degradation of the bioresorbable component. In some embodiments, the bioresorbable component may comprise collagen and oxidized, regenerated cellulose. In some embodiments, at least one of the degradation-modulating component may comprise a polymer having one or more monomeric repeating units. In some embodiments the monomeric repeating unit present in the polymer may be derived from another monomeric unit that has been modified, for example, functionalized, after polymerization. The monomeric repeating unit may comprise vinyl pyrrolidone, vinyl alcohol (for example, which may be derived from vinyl acetate), ethylene oxide, propylene oxide, ethylene glycol, acrylic acid, a salt of acrylic acid, an ester of acrylic acid, acrylamido methylpropane sulphonic acid, a salt of acrylamido methylpropane sulphonic acid, an ester of acrylamido methylpropane sulphonic acid, cellulose derivatives, copolymers thereof, blends or mixtures thereof, or combinations thereof.

For example, the polymer may be polyvinyl pyrrolidone, polyvinyl alcohol, polyethylene glycol, polypropylene glycol, poly(acrylic acid), or poly(acrylamido methylpropane sulphonic acid). The method may also comprise placing a sealing member over the dressing. The method may also comprise sealing the sealing member to tissue surrounding the tissue site to form a sealed space. The method may also comprise fluidly coupling a negative pressure source to the sealed space. The method may also comprise operating the negative pressure source to draw fluid from the tissue site and generate a negative pressure in the sealed space.

Objectives, advantages, and a preferred mode of making and using the claimed subject matter may be understood best by reference to the accompanying drawings in conjunction with the following detailed description of illustrative embodiments.

It should be noted that the figures set forth herein are intended to illustrate the general characteristics of certain example embodiments. The figures may not precisely reflect the characteristics of any given embodiment, and are not necessarily intended to define or limit the scope of the claimed subject matter.

DESCRIPTION OF EXAMPLE EMBODIMENTS

The following description of example embodiments provides information that enables a person skilled in the art to make and use the subject matter set forth in the appended claims, but may omit certain details already well-known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

Figure 1:
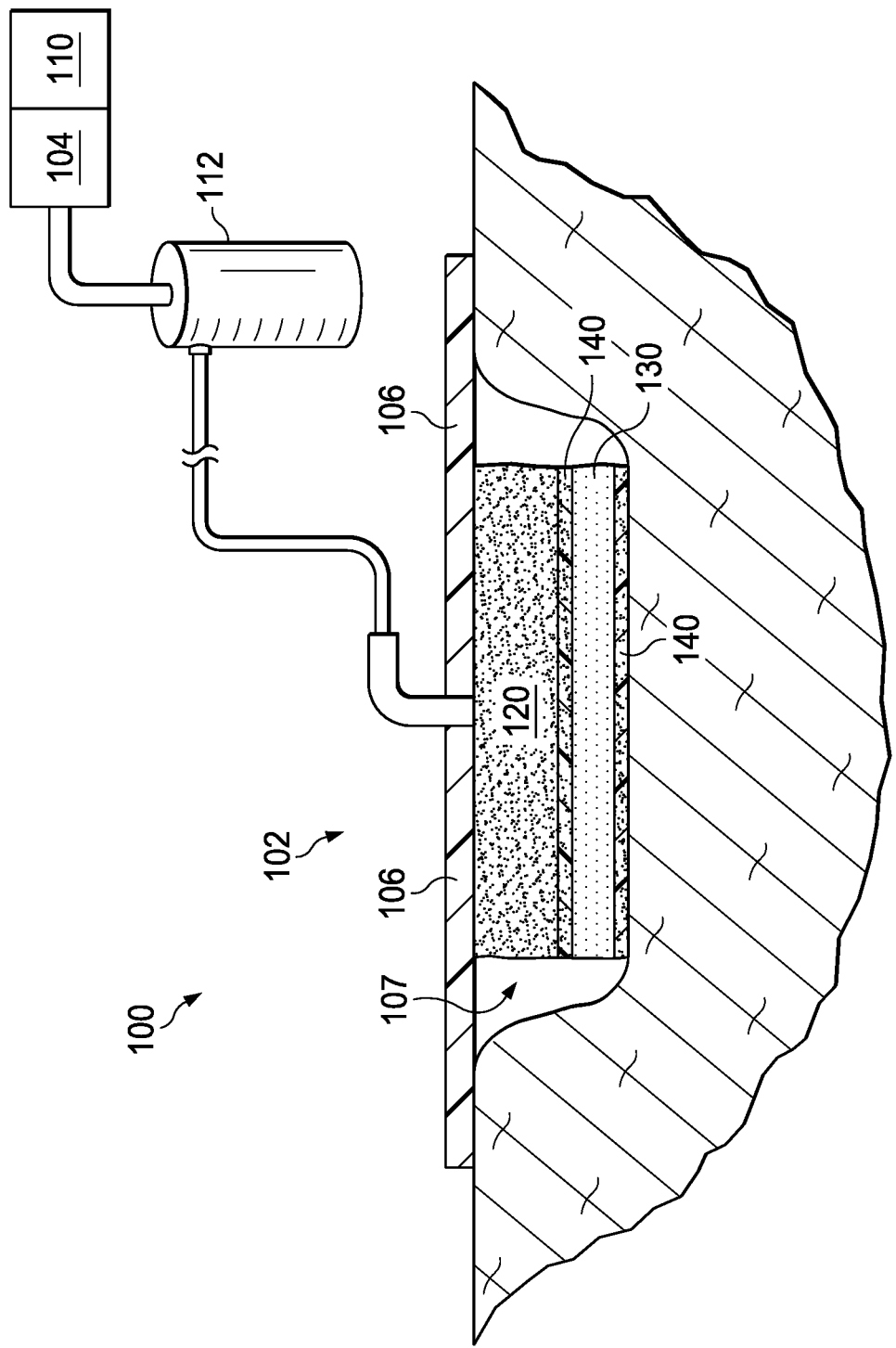
FIG. 1 is a simplified schematic of an example embodiment of a negative-pressure therapy system including a dressing in accordance with this specification.

For example, FIG. 1 illustrates an embodiment of a system 100 configured to provide negative pressure to a tissue site in accordance with the disclosure of this specification.

As used herein the term "tissue site" is intended to broadly refer to a wound, defect, or other treatment target located on or within tissue, including but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of any tissue that are not necessarily wounded or defective, but are instead areas in which it may be desirable to add or promote the growth of additional tissue.

In various embodiments, the system 100 generally includes a negative-pressure supply, and may include or be configured to be coupled to a distribution component, such as a dressing. In general, a distribution component may refer to any complementary or ancillary component configured to be fluidly coupled to a negative-pressure supply in a fluid path between a negative-pressure supply and a tissue site. A distribution component may be detachable and, as well, may be disposable, reusable, or recyclable. For example, in some embodiments, the system 100 may include a dressing 102 that is illustrative of a distribution component fluidly coupled to a negative-pressure source 104.

The fluid mechanics associated with using a negative-pressure source to reduce pressure in another component or location, such as within a sealed therapeutic environment, can be mathematically complex. However, the basic principles of fluid mechanics applicable to negative-pressure therapy are generally well-known to those skilled in the art. The process of reducing pressure may be described generally and illustratively herein as "delivering," "distributing," "providing," or "generating" negative pressure, for example.

In general, a fluid, such as wound fluid (for example, wound exudates and other fluids), flow toward lower pressure along a fluid path. Thus, the term "downstream" typically implies something in a fluid path relatively closer to a source of negative pressure or further away from a source of positive pressure. Conversely, the term "upstream" implies something relatively further away from a source of negative pressure or closer to a source of positive pressure. Similarly, it may be convenient to describe certain features in terms of a fluid "inlet" or "outlet" in such a frame of reference. This orientation is generally presumed for purposes of describing various features and components herein. However, the fluid path may also be reversed in some applications (such as by substituting a positive-pressure source for a negative-pressure source) and this descriptive convention should not be construed as a limiting convention.

As used herein, "negative pressure" is generally intended to refer to a pressure less than a local ambient pressure, such as the ambient pressure in a local environment external to a sealed therapeutic environment provided by the dressing 102. In many cases, the local ambient pressure may also be the atmospheric pressure proximate to or about a tissue site. Alternatively, the pressure may be less than a hydrostatic pressure associated with the tissue at the tissue site. Unless otherwise indicated, values of pressure stated herein are gauge pressures. Similarly, references to increases in negative pressure typically refer to a decrease in absolute pressure (e.g., a "more negative" pressure), while decreases in negative pressure typically refer to an increase in absolute pressure (e.g., a "less negative" pressure or a "more positive" pressure). While the amount and nature of negative pressure applied to a tissue site may vary according to therapeutic requirements, the pressure is generally a low vacuum, also commonly referred to as a rough vacuum, between −5 mm Hg (−667 Pa) and −500 mm Hg (−66.7 kPa). Common therapeutic ranges are between −50 mm Hg (−6.7 kPa) and −300 mm Hg (−39.9 kPa).

In various embodiments, a negative-pressure supply, such as the negative-pressure source 104, may be a reservoir of air at a negative pressure, or may be a manual or electricallypowered device that can reduce the pressure in a sealed volume, such as a vacuum pump, a suction pump, a wall suction port available at many healthcare facilities, or a micro-pump, for example. A negative-pressure supply may be housed within or used in conjunction with other components, such as sensors, processing units, alarm indicators, memory, databases, software, display devices, or user interfaces that further facilitate therapy. For example, in some embodiments, the negative-pressure source may be combined with one or more other components into a therapy unit. A negative-pressure supply may also have one or more supply ports configured to facilitate coupling and de-coupling of the negative-pressure supply to one or more distribution components.

In some embodiments, the system 100 may include a controller 110. The controller 110 may also be coupled to the negative-pressure source 104. The controller 110 may generally be configured to control one or more operational parameters associated with the negative-pressure therapy system. In some embodiments, the system 100 may include one or more sensors, for example, to measure operating parameters and provide feedback signals indicative of those operating parameters to a controller like the controller 110. A controller, such as the controller 110, may be a microprocessor or computer programmed to operate one or more components of the system 100, such as the negative-pressure source 104. In some embodiments, for example, the controller 110 may be a microcontroller, which generally comprises an integrated circuit containing a processor core and a memory programmed to directly or indirectly control one or more operating parameters of the system 100. Operating parameters may include the power applied to the negative-pressure source 104, the pressure generated by the negative-pressure source 104, or the pressure distributed to the dressing 102, for example. The controller 110 may also be configured to receive one or more input signals, such as an input signal from a user interface.

In some embodiments, the negative-pressure source 104 may be operatively coupled to the dressing 102 via a dressing interface. In some embodiments, the system 100 may include a fluid container, such as a container 112, fluidly coupled to the dressing 102 and to the negative-pressure source 104. The container 112 is representative of a container, canister, pouch, or other storage component, which can be used to manage exudates and other fluids withdrawn from a tissue site. In many environments, a rigid container may be preferred or required for collecting, storing, and disposing of fluids. In other environments, fluids may be properly disposed of without rigid container storage, and a re-usable container could reduce waste and costs associated with negative-pressure therapy.

In various embodiments, components may be fluidly coupled to each other to provide a path for transferring fluids (i.e., liquid and/or gas) between the components. For example, components may be fluidly coupled through a fluid conductor, such as a tube. As used herein, the term "tube" is intended to broadly include a tube, pipe, hose, conduit, or other structure with one or more lumina adapted to convey a fluid between two ends thereof. Typically, a tube is an elongated, cylindrical structure with some flexibility, but the geometry and rigidity may vary. In some embodiments, two or more components may also be coupled by virtue of physical proximity, being integral to a single structure, or being formed from the same piece of material. Moreover, some fluid conductors may be molded into or otherwise integrally combined with other components. Coupling may also include mechanical, thermal, electrical, or chemical coupling (such as a chemical bond) in some contexts. For example, a tube may mechanically and fluidly couple the dressing 102 to the container 112 in some embodiments. In general, components of the system 100 may be coupled directly or indirectly. For example, the negative-pressure source 104 may be directly coupled to the controller 110, and may be indirectly coupled to the dressing 102, for example, through the container 112.

Dressing

Often, in the context of negative-pressure therapy, negative pressure may be applied to a tissue site via materials and devices generally characterized as "dressings." Generally, in addition to providing for the application of negative pressure to a tissue site, dressings may control bleeding, ease pain, assist in debriding, protect tissue from infection, modulate protease activity, or otherwise promote healing and protect the tissue site from damage.

In some embodiments, the fluid pathways of a manifold may be interconnected to improve distribution or collection of fluids. In some embodiments, a manifold may be a porous foam material having a plurality of interconnected cells or pores. For example, open-cell foams, including reticulated foams, generally include pores, edges, and/or walls adapted to form interconnected fluid pathways, such as channels. In various embodiments, foam-forming materials may be formed into foam, such as by curing, so as to include various apertures and fluid pathways. In some embodiments, a manifold may additionally or alternatively comprise projections that form interconnected fluid pathways. For example, a manifold may be molded to provide surface projections that define interconnected fluid pathways.

In various embodiments, the dressing 102 may be generally configured to distribute negative pressure, for example, so as to collect fluid. For example, the dressing 102 may comprise or be configured as a manifold. A "manifold" in this context generally includes any composition or structure providing a plurality of pathways configured to collect or distribute fluid across a tissue site under pressure. For example, a manifold may be configured to receive negative pressure from a negative-pressure source and to distribute negative pressure through multiple apertures (pores), which may have the effect of collecting fluid and drawing the fluid toward the negative-pressure source. For example, in some embodiments the dressing 102 may be configured to receive negative pressure from the negative-pressure source 104 and to distribute the negative pressure through a sealed space 107, for example, which may have the effect of collecting fluid from the tissue site. In additional or alternative embodiments, the fluid path may be reversed or a secondary fluid path may be provided to facilitate movement of fluid across a tissue site.

In some embodiments, a dressing may generally comprise one or more components configured to interface with a tissue site or to perform any of a variety of functions. For example, in some embodiments the dressing 102 may comprise a cover 106 and a manifold 120. The dressing 102 may also comprise at least one bioresorbable component 130, at least one degradation-modulating component 140, or some combination of at least one bioresorbable component 130 and at least one degradation-modulating component 140. In some embodiments, the dressing 102 may comprise one, two, three, four, five, six, seven, eight, or more bioresorbable components 130. Also, in some embodiments, the dressing 102 may comprise one, two, three, four, five, six, seven, eight, or more degradation-modulating components 140. In various embodiments, the bioresorbable component 130 and the degradation-modulating component 140 may be present in any suitable number of layers. For example, in some embodiments, the bioresorbable component 130 and the degradation-modulating component 140 may be present as separate layers. In some embodiments the bioresorbable component 130 and the degradation-modulating component 140 may be incorporated within a single layer.

Dressing—Cover

In various embodiments, the cover 106 may generally be configured to provide a bacterial barrier and protection from physical trauma. The cover 106 may also be constructed from a material that can reduce evaporative losses and provide a fluid seal between two components or two environments, such as between a therapeutic environment and a local external environment. The cover 106 may be, for example, an elastomeric film or membrane that can provide a seal adequate to maintain a negative pressure at a tissue site for a given negative-pressure source. In some embodiments, the cover 106 may have a high moisture-vapor transmission rate (MVTR). For example, the MVTR may be at least 300 g/m$^2$ per twenty-four hours. In some embodiments, the cover 106 may be formed from a suitable polymer. For example, the cover 106 may comprise a polymer drape, such as a polyurethane film, which may be permeable to water vapor but generally impermeable to liquid. In such embodiments, the cover 106 may have a thickness in the range of about from 25 to about 50 microns. In embodiments where the cover comprises a permeable material, the cover 106 may have a sufficiently low permeability that a desired negative pressure may be maintained.

In some embodiments, the cover 106 may be configured to be attached to an attachment surface, such as undamaged epidermis, a gasket, or another cover, for example, via an attachment device. For example, in some embodiments the cover may be attached to epidermis so as to form the sealed space 107. In such an embodiment, the attachment device may take any suitable form. For example, an attachment device may be a medically-acceptable, pressure-sensitive adhesive that extends about a periphery, a portion, or an entire sealing member. In some embodiments, for example, some or all of the cover 106 may be coated with an adhesive, such as an acrylic adhesive, having a coating weight between 25-65 grams per square meter (g.s.m.). Thicker adhesives, or combinations of adhesives, may be applied in some embodiments, for example, to improve the seal and reduce leaks. Other example embodiments of an attachment device may include a double-sided tape, a paste, a hydrocolloid, a hydrogel, a silicone gel, or an organogel.

Dressing—Manifold

In some embodiments, the manifold 120 may comprise or consist essentially of foam, for example, a reticulated foam, or combinations thereof. In various embodiments, the average pore size of the foam may vary according to needs of a prescribed therapy. The tensile strength of the manifold 120 may also vary according to needs of a prescribed therapy.

In some embodiments, the manifold 120 may be foam characterized by density. In some embodiments, the manifold 120 may be characterized as a relatively dense material. For example, in various embodiments, the manifold 120 may have a density of from about 24 kg/m$^3$ to about 125 kg/m$^3$ or, in a more particular embodiment, from about 24 kg/m$^3$ to about 72 kg/m$^3$. Additionally or alternatively, the manifold 120 may also be characterized as exhibiting a particular porosity and/or pore size. The number of pores and the average pore size of the manifold 120 may vary according to needs of a prescribed therapy. For example, in various embodiments, the manifold 120 may be characterized as exhibiting a porosity of from about 20 pores per inch to about 120 pores per inch. Additionally, in various embodiments, the manifold 120 may have an average pore size in a range of from about 400 to about 600 microns.

In some embodiments, the manifold 120 may be characterized as hydrophobic. For example, the manifold 120 may be characterized as a hydrophobic, open-cell foam. Not intending to be bound by theory, in such embodiments, the hydrophobic characteristics may prevent the manifold 120 from directly absorbing fluid, such as wound exudate from a tissue site, but may allow the fluid to pass, for example, through the internal structure. For example, in some embodiments, the manifold 120 may be a hydrophobic, open-cell polyurethane foam, a silicone foam, a polyether block amide foam, such as PEBAX®, an acrylic foam, a polyvinyl chloride (PVC) foam, a polyolefin foam, a polyester foam, a polyamide foam, a thermoplastic elastomer (TPE) foam such as a thermoplastic vulcanizate (TPV) foam, other crosslinked elastomeric foams such as foams formed from styrene-butadiene rubber (SBR) and ethylene propylene diene monomer (EPDM) rubber, or combinations thereof. Examples of a foam suitable for use as the manifold 120 include the foam used in the V.A.C.® GRANUFOAM™ Dressing commercially-available from KCI in San Antonio, Tex.

In some alternative embodiments, the manifold 120 may be characterized as hydrophilic. Not intending to be bound by theory, in such embodiments, the manifold 120 may be effective to wick fluid while also continuing to distribute negative pressure to a tissue site. In such embodiments, the wicking properties of the manifold 120 may draw fluid away from a tissue site by capillary flow or other wicking mechanisms. An example of hydrophilic foam may include a polyvinyl alcohol or polyether, open-cell foam. Other foams that may exhibit hydrophilic characteristics include hydrophobic foams that have been treated or coated to provide hydrophilicity. For example, the manifold 120 may be a treated open-cell polyurethane foam.

Bioresorbable Component

In some embodiments, the bioresorbable component 130 may be characterized as biodegradable or as exhibiting biodegradability. As used herein, "biodegradable" and "biodegradability" may refer to a characteristic of a material to at least partially break down upon exposure to physiological fluids or processes. For example, in some embodiments, the bioresorbable component 130 may disintegrate, degrade, or dissolve when contacted with an aqueous medium, such as water, blood, or wound exudate from a tissue site.

Biodegradability may be a result of a chemical process or condition, a physical process or condition, or combinations thereof.

Additionally or alternatively, in some embodiments, the bioresorbable component 130 may be characterized as bioresorbable or as exhibiting bioresorbability. As used herein, "bioresorbable" and "bioresorbability" may refer to a characteristic of a material to be broken down into degradation products that may be absorbed at a tissue site so as to be eliminated by the body, for example via metabolism or excretion. In some embodiments the bioresorbability characteristics of the bioresorbable component 130 may be such that at least a portion of the bioresorbable component 130 or the material from which the bioresorbable component 130 is formed may be eliminated from the tissue site to which it is applied by bioresorption.

In some embodiments, the bioresorbable component 130 may be configured to exhibit a particular proportion of disintegration, degradation, or dissolution within a particular time period. For instance, in various embodiments, the bioresorbable component 130 may be configured such that about 90% by weight, or about 95% by weight, or about 99% by weight, or about 100% by weight of a particular bioresorbable component 130 may be disintegrated, degraded, or dissolved within a time period of from about 6 hours to about 48 hours, or from about 12 hours to about 36 hours, or from about 18 hours to about 24 hours, from contact with a physiological fluid, for example, an aqueous fluid such as blood or wound exudate, at a temperature of about 37° C.

In some embodiments, the bioresorbable component 130 may comprise a suitable structure, for example, a film, foam such as open-cell foam, a fibrous substrate such as a woven or non-woven mesh, or combinations thereof. In various embodiments, suitable foam may an average pore size that can vary according to needs of a prescribed therapy. For example, the bioresorbable component 130 may comprise foam having pore sizes in a range of 400-600 microns. Additionally, a suitable film or foam may have various physical properties, such as tensile strength, as will be suitable according to needs of a prescribed therapy.

In some embodiments, the bioresorbable component 130 may comprise or be formed at least partially from a suitable composition, which may be referred to herein as a bioresorbable composition. For example, the bioresorbable composition may make up at least some part of an open-cell foam or film of the bioresorbable component 130.

In some embodiments, the bioresorbable composition comprises oxidized cellulose or, in a more particular embodiment, oxidized regenerated cellulose (ORC). Oxidized cellulose may be produced by the oxidation of cellulose, for example with dinitrogen tetroxide. Not intending to be bound by theory, this process may convert primary alcohol groups on the saccharide residues to carboxylic acid group, forming uronic acid residues within the cellulose chain. The oxidation may not proceed with complete selectivity, and as a result hydroxyl groups on carbons 2 and 3 may be converted to the keto form. These ketone units yield an alkali labile link, which at pH 7 or higher initiates the decomposition of the polymer via formation of a lactone and sugar ring cleavage. As a result, oxidized cellulose may be biodegradable and bioresorbable under physiological conditions.

In some embodiments, the oxidized cellulose may be ORC prepared by oxidation of a regenerated cellulose, such as rayon. ORC may be manufactured, for example, by the process described in U.S. Pat. No. 3,122,479 to Smith, issued Feb. 24, 1964, which is incorporated herein by reference in its entirety. ORC is available with varying degrees of oxidation and hence rates of degradation. In some embodiments, the ORC may be in the form of water-soluble low molecular weight fragments obtained by alkali hydrolysis of ORC.

The ORC may be used in a variety of physical forms, including particles, fibers, sheets, sponges, or fabrics. In some embodiments, the ORC is in the form of particles, such as fiber particles or powder particles, for example dispersed in a suitable solid or semisolid topical medicament vehicle. In some embodiments, the bioresorbable composition comprises ORC fibers, for example, having a volume fraction of at least 80% of the fibers have lengths in the range of from about 20 μm to about 50 mm. In some embodiments, a volume fraction of at least 80% of the fibers have lengths in the range of from about 5 μm to about 1000 μm, or from about 250 μm to about 450 μm. In some embodiments, a volume fraction of at least 80% of the fibers have lengths in the range of from about 25 mm to about 50 mm. Desired size distributions can be achieved, for example, by milling an ORC cloth, followed by sieving the milled powder to remove fibers outside the range. Fabrics may include woven, non-woven and knitted fabrics.

The ORC may be present in the bioresorbable composition at any level appropriate to result in the desired absorbency and rheological characteristics of the bioresorbable composition and/or the bioresorbable component. For example, the ORC may be present in the bioresorbable component at a level of from about 10% to about 80% by weight, or from about 30% to about 60% by weight, or from about 40% to about 50% by weight, or about 45% ORC by weight of the bioresorbable component.

In some embodiments, the bioresorbable composition comprises a structural protein. Examples of suitable structural proteins may include, but are not limited to fibronectin, fibrin, laminin, elastin, collagen, gelatins, keratin, and mixtures thereof. For instance, in a particular embodiment, the structural protein comprises, or is, collagen. The collagen may be obtained from any natural source. The collagen may be Type I, II or III collagen, or may also be chemically modified collagen, for example, an atelocollagen obtained by removing the immunogenic telopeptides from natural collagen. The collagen may also comprise solubilized collagen or soluble collagen fragments having molecular weights in the range of from about 5,000 to about 100,000 or from about 10,000 to about 50,000, which may be obtained, for example, by pepsin treatment of natural collagen. In various embodiments, the collagen is obtained from bovine corium that has been rendered largely free of non-collagenous components. Such non-collagenous components include fat, non-collagenous proteins, polysaccharides and other carbohydrates, as described in U.S. Pat. No. 4,614,794, Easton et al., issued Sep. 30, 1986 and U.S. Pat. No. 4,320,201, Berg et al., issued Mar. 16, 1982, incorporated by reference herein.

The collagen or other structural protein may be present in the bioresorbable composition at any level appropriate. For example, the collagen or other structural protein may be present in the bioresorbable composition at a level of from about 20% to about 90% by weight, or from about 40% to about 70% by weight, or from about 50% to about 60%, or about 55% collagen by weight of the bioresorbable component.

In some, more particular embodiments, the bioresorbable composition comprises both ORC and collagen. For example, in some embodiments, the bioresorbable component comprises ORC at a level of from about 40% to about 50%, or about 45%, and collagen at a level of from about 50% to about 60%, or about 55%, by weight of the bioresorbable component.

Additionally, in some embodiments the bioresorbable composition may comprise one or more additional, optional materials. Such optional components may include, for example, preservatives, stabilizing agents, hydrogels and other gelling agents, plasticizers, matrix strengthening materials, dyestuffs, and various active ingredients. In various embodiments, the additional, optional materials may each, when present, be present in a safe and effective amount. As referred to herein, a "safe and effective" amount of a material used herein, refers to an amount that is sufficient to impart a desired effect without undue adverse side effects (such as toxicity, irritation, or allergic response), commensurate with a reasonable benefit/risk ratio when used in the manner of this technology. The specific safe and effective amount of a particular material may vary with such factors as the type and quantity of other materials in the composition, the intended use, and the physical condition of the subject to whom the bioresorbable compositions are given, and the form in which the bioresorbable compositions are employed.

For example, in some embodiments, the bioresorbable composition may comprise an optional gelling agent, examples of which may include, but are not limited to polyurethane gels, modified acrylamide polymers, and hydrophilic polysaccharides. Examples of hydrophilic polysaccharides may include, but are not limited to, alginates, chitosan, chitin, guar gums, pectin, polyethylene glycols, dextrans, starch derivatives, cellulose derivatives (such as hydroxyethyl cellulose, hydroxylpropyl cellulose, and hydroxypropylmethyl cellulose), glycosaminoglycans, galactomannans, chondroitin salts (such as chondroitin sulfate), heparin salts (such as heparin sulfate), hyaluroinic acid and salts thereof, hyaluronates, and mixtures thereof.

In some embodiments, the bioresorbable composition may comprise carboxymethyl cellulose ("CMC"), for example, to modify the rheological, absorbency, or other characteristics of the bioresorbable composition or the bioresorbable component. The CMC may be derived from cellulose and modified such that carboxymethyl groups are bonded to hydroxyl groups in the glucopyranose monomers that make up the cellulose. The CMC may be in salt form, for example, comprising a physiologically acceptable cation, such as sodium (i.e., sodium carboxymethyl cellulose). CMC is commercially available as Walocel™ (sold by The Dow Chemical Company) and Cekol® (sold by CP Kelco). When present, the CMC may be present in the bioresorbable composition at any level appropriate to result in the desired characteristics.

In some embodiments, the bioresorbable composition comprises a strengthening material, which can improve the handling characteristics of a bioresorbable component 130. For example, a strengthening material can decrease a substrate's susceptibility to tearing. An example of a suitable strengthening material includes non-gelling cellulose fibers. Such "non-gelling" cellulose fibers may be substantially water-insoluble, and may be produced from cellulose that has not been chemically modified to increase water solubility (as contrasted from carboxymethyl cellulose or other cellulose ethers). Non-gelling cellulose fibers are commercially available as Tencel® fibers (sold by Lenzing AG). Such fibers may be processed from a commercially-available continuous length, by cutting into lengths that are, in some embodiments, from about 0.5 to about 5 cm, or from about 2 to about 3 cm in length. The non-gelling cellulose fibers may be present in the bioresorbable composition at any level appropriate to result in the desired physical characteristics of the bioresorbable component.

In some embodiments, the bioresorbable composition may also comprise one or more active ingredients, for example, which aid in wound healing. Examples of active ingredients include, but are not limited to, non-steroidal anti-inflammatory drugs, acetaminophen, steroids, optional antibiotics and antiseptics (e.g., silver and chlorhexidine), growth factors (e.g. fibroblast growth factor or platelet derived growth factor), peptides, and microRNA. In general, such active ingredients, when present may be present at a level of from about 0.1% to about 10% by weight. As an example, the bioresorbable composition may comprise a growth factor. Examples of suitable growth factors include, but are not limited to, platelet derived growth factor (PDGF), fibroblast growth factor (FGF), and epidermal growth factor (EGF), and mixtures thereof.

For example, the bioresorbable composition may comprise an antimicrobial agent, an antiseptic, or both. Examples of antimicrobial agents include, but are not limited to, tetracycline, penicillins, terramycins, erythromycin, bacitracin, neomycin, polymycin B, mupirocin, clindamycin, and combinations thereof. Examples of antiseptics include, but are not limited to silver, polyhexanide (polyhexamethylene biguanide or PHMB), chlorhexidine, povidone iodine, triclosan, sucralfate, quaternary ammonium salts, and combinations thereof. For example, in various embodiments, the bioresorbable composition may comprise silver, which may be in metallic form, in ionic form (e.g., a silver salt), or both. For example, the silver may be present in ionic form. In some embodiments, the bioresorbable composition may comprise a complex of silver and ORC (a "Silver/ORC complex"). As referred to herein, such a complex may refer to an intimate mixture at the molecular level, for example, with ionic or covalent bonding between the silver and the ORC. For example, the Silver/ORC complex may comprise a salt formed between the ORC and $Ag^+$, but it may also comprise silver clusters or colloidal silver metal, for example produced by exposure of the complex to light. The complex of an anionic polysaccharide and silver can be made by treating the ORC with a solution of a silver salt. In various embodiments, the silver salt may be the salt of silver with a weak acid. Silver/ORC complexes useful herein, and methods of producing such complexes, are described in U.S. Pat. No. 8,461,410, Cullen et al., issued Jun. 11, 2013, incorporated by reference herein. Similar processes are described in U.S. Pat. No. 5,134,229, Saferstein et al., issued Jul. 28, 1992, incorporated by reference herein. In various embodiments, the Silver/ORC Complex may be present in the bioresorbable component at a level of from about 1% to about 2% by weight of the bioresorbable component. Alternatively, in other embodiments, the bioresorbable composition does not contain an antimicrobial agent or an antiseptic.

In some embodiments, such as in embodiments where the bioresorbable composition comprises silver, the bioresorbable composition may comprise a dyestuff. The dyestuff may be light-absorbing in the visible region 400-700 nm. Such dyestuffs may be operable to photochemically trap generated free radicals that could otherwise react with the silver in the present compositions, acting as photochemical desensitisers. In various embodiments, the antioxidant dyestuff may be selected from the group consisting of aniline dyes, acridine dyes, thionine dyes, bis-naphthalene dyes, thiazine dyes, azo dyes, anthraquinone dyes, and mixtures thereof. For example, the antioxidant dyestuff may be selected from the group consisting of gentian violet, aniline blue, methylene blue, crystal-violet, acriflavine, 9-aminoacridine, acridine yellow, acridine orange, proflavin, quinacrine, brilliant green, trypan blue, trypan red, malachite green, azacrine, methyl violet, methyl orange, methyl yellow, ethyl violet, acid orange, acid yellow, acid blue, acid red, thioflavin, alphazurine, indigo blue, methylene green, and mixtures thereof. If present, the dyestuff may be present in the bioresorbable component at a level of about 0.05% to about 5%, or about 0.2% to about 2% by weight of the bioresorbable component.

In some embodiments, the bioresorbable composition may be configured to exhibit or impart one or more beneficial or adverse effects when deployed in a physiological environment (e.g., a tissue site), for example, protease-inhibiting activity, antimicrobial activity, or combinations thereof. For example, in some embodiments, the bioresorbable component 130 may be configured to modulate protease activity. For example, contact with a wound fluid, such as wound exudate, may cause the bioresorbable component 130 to break down into products that may have the effect of modulating protease activity. Modulating protease activity may include inhibiting protease activity, in some embodiments. For example, the disintegration, degradation, and/or dissolution products of collagen and/or ORC may be effective to inhibit the activity of destructive enzymes such as neutrophil elastase and matrix metalloproteinase (MMP). In various embodiments, the bioresorbable component 130 may be effective to inhibit protease activity such that protease activity is decreased to less than about 75% of the protease activity than would be present if uninhibited, or to less than about 50%, or to less than about 40%, or to less than about 30% to less than about 20% of the protease activity that would be present if uninhibited.

In various embodiments, the bioresorbable composition may be essentially free of water. For example, in some embodiments, the bioresorbable composition contains 10% or less, 8% or less, or 5% or less, of water. In some embodiments, the bioresorbable component 130 may be freeze dried, such as through lyophilization, for example.

Degradation-Modulating Component

Generally, in some embodiments, the degradation-modulating component 140 may be configured to modulate degradation of the bioresorbable component 130. Modulating degradation may include controlling, regulating, delaying, impeding, reducing, increasing, or encouraging degradation, or combinations thereof, for example, for a period of time after the dressing 102 is positioned with respect to a tissue site.

In some embodiments the degradation-modulating component 140 may be configured to modulate the communication of a physiological fluid, such as wound exudate or blood, from an environment to the bioresorbable component 130. Not intending to be bound by theory, by modulating the communication of a physiological fluid to the bioresorbable component 130, the degradation-modulating component 140 may be effective to modulate the degradation of the bioresorbable component 130. For example, in some embodiments, the degradation-modulating component 140 may comprise, be configured as, or otherwise form a structural barrier to fluid communication to one or more surfaces of the bioresorbable component 130. Additionally or alternatively, the degradation-modulating component 140 may be configured as a structural support effective to physically support the bioresorbable component 130. Not intending to be bound by theory, by structurally supporting the bioresorbable component 130, the degradation-modulating component 140 may extend the duration over which the bioresorbable component 130 exhibits structural integrity.

In some embodiments, the degradation-modulating component 140 may be configured to modulate degradation of the bioresorbable component 130 for a predetermined interval, until a predetermined condition, or combinations thereof. In some embodiments, the degradation-modulating component 140 may be configured to control fluid communication to or from the bioresorbable component 130 and/or to structurally support the bioresorbable component 130 for a predetermined interval, until a predetermined condition, or combinations thereof.

In some embodiments, the degradation-modulating component 140 may comprise or be formed at least partially from a suitable composition, which may be referred to herein as a degradation-modulating composition. In some embodiments, the degradation-modulating composition may be further configured such that a degradation-modulating component 140 may, upon the passage of the predetermined interval and/or upon the occurrence of the predetermined condition, dissolve, dissociate, degrade, break down, undergo a structural change, or otherwise lose structural integrity, for example, such that the degradation-modulating component 140 does not continue to modulate degradation of the bioresorbable component 130.

In some embodiments, the degradation-modulating component 140 may be characterized as biodegradable and/or as exhibiting biodegradability. For example, in some embodiments, the degradation-modulating component 140 may be configured to exhibit a particular proportion of disintegration, degradation, or dissolution within a particular time period. For instance, in various embodiments the degradation-modulating component 140 may be configured such that about 90% by weight, or about 95% by weight, or about 99% by weight, or about 100% by weight of the degradation-modulating component 140 may be disintegrated, degraded, or dissolved within a time period of from about 24 hours to about 150 hours, or from about 36 hours to about 120 hours, or from about 48 hours to about 96 hours, from contact with a physiological fluid, for example, an aqueous fluid such as blood or wound exudate, at a temperature of about 37° C. In some embodiments, the degradation-modulating component 140 may be configured to disintegrate, degrade, or dissolve over an extended duration relative to the bioresorbable component 130. For example, the degradation-modulating component 140 may be configured to disintegrate, degrade, or dissolve, at a slower rate than the bioresorbable component 130, for example, such that a given volume of the degradation-modulating component 140 may be configured to disintegrate, degrade, or dissolve over a duration that is greater than a duration over which the same volume of the bioresorbable component 130 will disintegrate, degrade, or dissolve. For example, the degradation-modulating component 140 may be configured to disintegrate, degrade, or dissolve at a rate that is less than about 70%, or less than about 60%, or less than about 50%, or less than about 40%, or less than about 30%, or less than about 20 of a rate at which the bioresorbable component 130 will disintegrate, degrade, or dissolve.

Additionally or alternatively, in some embodiments the degradation-modulating component 140 may be configured to exhibit a particular proportion of disintegration, degradation, or dissolution upon the occurrence of a predetermined condition, such as when present within an environment including an enzyme, for example, a protease. In such an embodiment, the degradation-modulating component 140 may be configured to exhibit an increased rate of disintegration, degradation, or dissolution in the presence of protease, for example, the degradation-modulating component may be configured to disintegrate, degrade, or dissolve at about 10% less time than in the absence of a protease, or about 20% less time, or about 25% less time, or about 30% less time, or about 35% less time, or about 40% less time, or about 45% less time, or about 50% less time.

In some embodiments, the degradation-modulating composition may comprise a polymer configured to dissolve, dissociate, degrade, break, undergo a structural change, or otherwise lose structural integrity, upon passage of the predetermined interval and/or upon the occurrence of the predetermined condition. The dissolution, dissociation, degradation, breakage, occurrence of a structural change, or other loss of structural integrity of the polymer may be the result of various physical and/or chemical reactions, for example, degradation of polymer backbone, degradation or alteration of polymeric side-chains, loss of cross-linking between polymer chains, state changes of the polymer (e.g., becoming a gel, becoming liquideous, dissolving in another liquid, swelling, or the like), or combinations thereof. For example, the degradation-modulating composition may comprise a polymer that is water-soluble.

The term "polymer" may refer generally to the combined products of a single chemical polymerization reaction. For example, polymers may be produced by combining monomeric subunits into a covalently bonded chain. Polymers generally including a single type of monomeric repeating unit may be referred to as "homopolymers," and polymers including two or more types of monomeric repeating units may be referred to as "copolymers." For example, the term "copolymer" may include products that are obtained by copolymerization of two monomeric species, those obtained from three monomeric species (e.g., terpolymers), those obtained from four monomeric species (e.g., quaterpolymers), etc. In various embodiments, a polymer may have different regions along its length, for example, differing as to the arrangement of the component monomer units.

In some embodiments, suitable examples of polymers that may be included in the degradation-modulating composition forming or partially-forming the degradation-modulating component 140 may include those polymers having one or more suitable monomeric units. In some embodiments the monomeric unit present in the polymer may be derived from another monomeric unit that has been modified, for example, functionalized, after polymerization. In some embodiments, the monomeric unit may comprise vinyl pyrrolidone, vinyl alcohol (for example, which may be derived from vinyl acetate), ethylene oxide, propylene oxide, ethylene glycol, acrylic acid, a salt of acrylic acid, an ester of acrylic acid, acrylamido methylpropane sulphonic acid, a salt of acrylamido methylpropane sulphonic acid, an ester of acrylamido methylpropane sulphonic acid, cellulose derivatives, copolymers thereof, blends or mixtures thereof, and combinations thereof. In some embodiments, these monomeric units may be present as a repeating unit or, additionally or alternatively, the monomeric unit may be present in a repeating unit comprising two, three, or more monomers, for example, as part of a dimer, trimer, or other oligomer. The term "repeating unit" generally refers to a fragment of a polymer that, when repeated, forms at least a portion of a polymer chain, for example, a single repeated monomer residue or a repeated sequence of two or more monomer residues. In some embodiments, at least a portion of the polymers that may be included in the degradation-modulating composition forming or partially-forming the degradation-modulating component may be cross-linked. For example, the polymer may comprise polyvinyl pyrrolidone, polyvinyl alcohol, polyethylene glycol, polypropylene glycol, poly(acrylic acid), or poly(acrylamido methylpropane sulphonic acid).

In some embodiments, the polymers that may be included in the degradation-modulating composition forming or partially-forming the degradation-modulating component may be characterized as having a non-crosslinked, average molecular mass in the range of from about 25,000 Daltons to about 2,000,000 Daltons, or from about 50,000 Daltons to about 1,000,000 Daltons, or from about 75,000 Daltons to about 750,000 Daltons. Additionally or alternatively, in some embodiments the polymers that may be included in the degradation-modulating composition forming or partially-forming the degradation-modulating component may be characterized as having an average number of repeating units ranging from about 10 to 50,000, or from about 1,000 to about 40,000, or from about 2,500 to about 30,000.

Configurations of Bioresorbable Component and Degradation-Modulating Component

In various embodiments, the bioresorbable component 130 and the degradation-modulating component 140 may have any suitable configuration. For example, in some embodiments, the bioresorbable component 130 and the degradation-modulating component 140 may be present in separate, distinct layers. In some embodiments, a separate and distinct layer of the degradation-modulating component 140 may be positioned adjacent to at least one bioresorbable component 130, which may also be configured as a separate, distinct layer. For example, the degradation-modulating component 140 may at least partially cover or encapsulate the bioresorbable component 130. Additionally, in some embodiments, the degradation-modulating component 140 may also be configured to hold two adjacent bioresorbable components 130 together.

Figure 2:
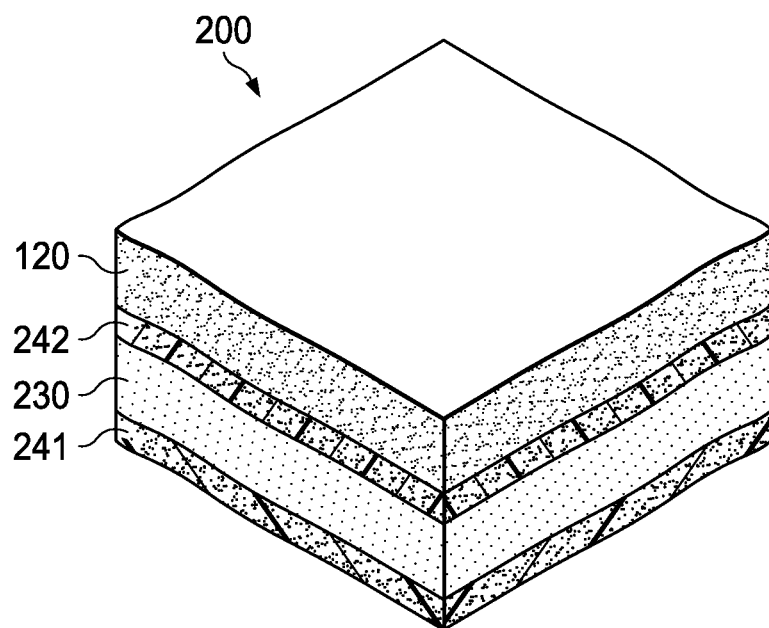
FIG. 2 is a partial cut-away view of an example embodiment of a dressing.

For example, FIG. 2 illustrates an embodiment of a dressing 200 comprising a manifold 120, two degradation-modulating components configured as a first degradation-modulating layer 241 and a second degradation-modulating layer 242, and a bioresorbable component configured as a bioresorbable layer 230. In the embodiment of FIG. 2, the first degradation-modulating layer 241 and the second degradation-modulating layer 242 may be positioned adjacent to the bioresorbable layer 230, for example, such that the first degradation-modulating layer 241 and the second degradation-modulating layer 242 may modulate the communication of a physiological fluid from a tissue site to one or more surfaces of the bioresorbable layer 230. In some embodiments, the first degradation-modulating layer 241, the second degradation-modulating layer 242, or both may comprise pores, perforations, apertures, or the like, for example, to allow fluid communication to the bioresorbable layer 230, for example, at a predetermined rate.

Figure 3:
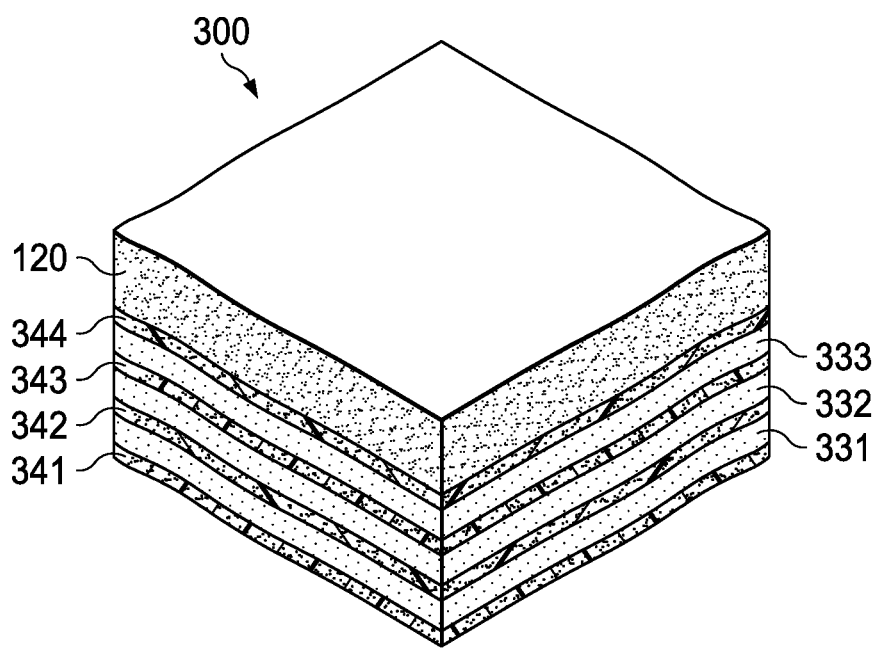
FIG. 3 is a partial cut-away view of an example embodiment of a dressing.

Additionally or alternatively, in some embodiments the dressing 102 may comprise any suitable number of degradation-modulating layers. For example, FIG. 3 illustrates an embodiment of a dressing 300 comprising a manifold 120, four degradation-modulating components configured as a first degradation-modulating layer 341, a second degradation-modulating layer 342, a third degradation-modulating layer 343, and a fourth degradation-modulating layer 344, and three bioresorbable components configured as a first bioresorbable layer 331, a second bioresorbable layer 332, and a third bioresorbable layer 333. In the embodiment of FIG. 3, the first degradation-modulating layer 341 and the second degradation-modulating layer 342 may be positioned adjacent to the first bioresorbable layer 331, for example, such that the first degradation-modulating layer 341 and the second degradation-modulating layer 342 may modulate the communication of a physiological fluid from a tissue site to surfaces of the first bioresorbable layer 331. Similarly, the second degradation-modulating layer 342 and the third degradation-modulating layer 343 may be positioned adjacent to the second bioresorbable layer 332, and the third degradation-modulating layer 343 and the fourth degradation-modulating layer 344 may be positioned adjacent to the third bioresorbable layer 333, for example, such that the second degradation-modulating layer 342, the third degradation-modulating layer 343, the fourth degradation-modulating layer 344 may modulate the communication of a physiological fluid from a tissue site to surfaces of the second bioresorbable layer 332 and the third bioresorbable layer 333. In some embodiments, the dressing 102 may similarly include any desired number of alternating degradation-modulating layers and bioresorbable layers, for example, such that a degradation-modulating layer is adjacent to one or more bioresorbable layers.

Figure 4:
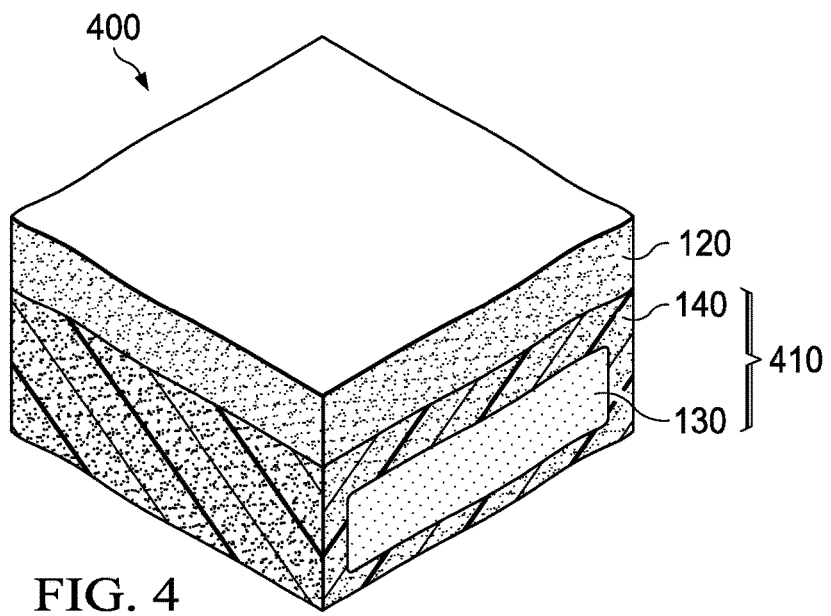
FIG. 4 is a partial cut-away view of an example embodiment of a dressing.

Additionally or alternatively, in some embodiments, the degradation-modulating component 140 may encapsulate the bioresorbable component 130, for example, to form a single layer. For example, FIG. 4 illustrates an embodiment of a dressing 400 comprising the bioresorbable component 130 encapsulated in the degradation-modulating component 140 to form a dressing layer 410. For example, the degradation-modulating component 140 may modulate the communication of a physiological fluid from a tissue site to the surfaces of the bioresorbable component 130.

Figure 5:
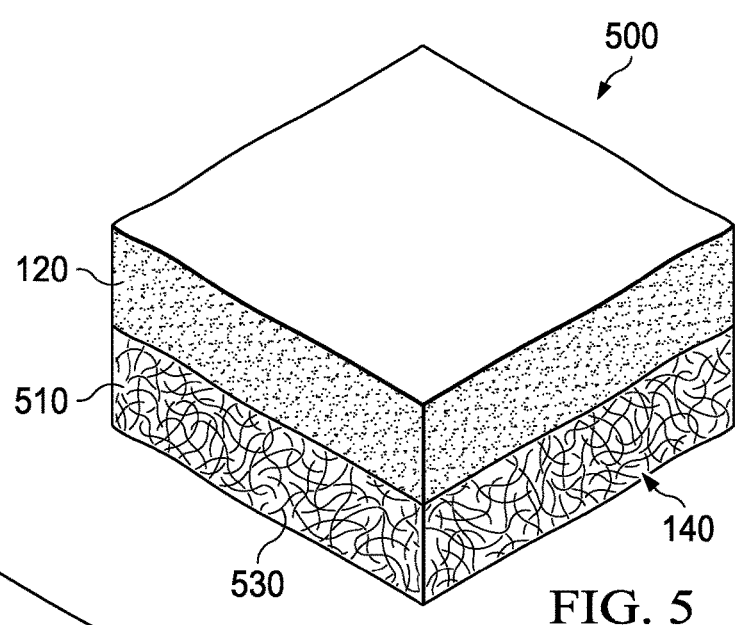
FIG. 5 is a partial cut-away view of an example embodiment of a dressing.

Additionally or alternatively, in some embodiments the bioresorbable component 130 may be incorporated within the degradation-modulating component 140. For example, the degradation-modulating component 140 may coat the bioresorbable component 130 in various particulate forms, such as fibers. For example, FIG. 5 illustrates an embodiment of a dressing 500 comprising a dressing layer 510 and the manifold 120. In the embodiment of FIG. 5, the bioresorbable component may be configured as fibers 530 in the dressing layer 510. The fibers 530 may be incorporated within the degradation-modulating component 140. For example, the degradation-modulating component 140 may comprise a coating on the fibers 530, and the coating can modulate the communication of a physiological fluid from a tissue site to the fibers 530.

Additionally or alternatively, in some embodiments the degradation-modulating component 140 may comprise, be configured as, or otherwise form a substrate or scaffold that may support the bioresorbable component 130. For example, in various embodiments, the degradation-modulating component 140 may comprise or be configured as a substrate such as a mesh, a lattice, a webbing, a woven or non-woven arrangement of fibers, or the like. The degradation-modulating component may be applied to or incorporated within the bioresorbable component 130.

Figure 6:
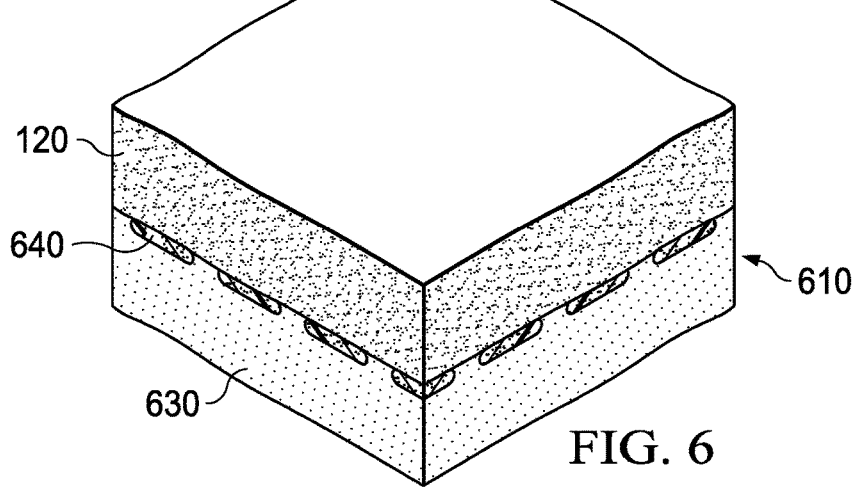
FIG. 6 is a partial cut-away view of an example embodiment of a dressing.

For example, FIG. 6 illustrates an embodiment of a dressing 600 comprising a dressing layer 610 and the manifold 120. In the embodiment of FIG. 6, the dressing layer 610 may comprise a degradation-modulating component configured as a scaffold 640. The dressing layer 610 may also comprise a bioresorbable component configured as a substrate 630 physically supported by the scaffold 640. For example, the scaffold 640 may be applied to and/or at least partially embedded within the substrate 630. For example, the scaffold 640 may regulate degradation, disintegration, or other losses of structural integrity of the substrate 630, for example, thereby regulating degradation of the bioresorbable component.

In various embodiments, the dressing 102 may comprise any suitable number of the bioresorbable components 130, for example, two, three, four, five, six, seven, or more bioresorbable components 130. In some embodiments, a configuration, composition, or other parameter of a given of the bioresorbable component 130 may be selected independently of, alternatively to, or dependent upon the configuration, composition, or other parameter of another of the bioresorbable component 130. For example, in some embodiments, the dressing 102 may be configured to provide a predetermined wear-time, such as a duration over which the bioresorbable component 130 present within the dressing 102 remain effective to provide biological activity, such as protease-inhibiting activity, antimicrobial activity, or combinations thereof.

For example, the predetermined wear-time of the dressing 102 may be varied dependent upon the number of bioresorbable components 130, the configuration of the various bioresorbable components 130, the number of degradation-modulating components 140, and the configuration of the various degradation-modulating components 140. Additionally, the predetermined interval after which a given degradation-modulating component 140 may be configured to dissolve, dissociate, degrade, break, undergo a structural change, or otherwise lose structural integrity may be manipulated by varying one or more parameters of that degradation-modulating component 140 and/or the degradation-modulating composition forming that degradation-modulating component 140. For example, various predetermined intervals may be achieved by manipulating thickness of the degradation-modulating component 140 the particular polymers or combination of polymers forming the degradation-modulating composition; the chain-length of the polymers forming the degradation-modulating composition; the presence or degree of cross-linking between various polymer chains within the degradation-modulating composition; or combinations thereof. In various embodiments, the dressing may be configurable to provide a wear-time from about 3 days to about 12 days, or from about 5 days to about 10 days, or from about 6 days to about 8 days.

Methods

In operation, for example, in the context of a negative-pressure therapy, the dressing 102 may be placed within, over, on, or otherwise proximate to a tissue site, for example, a wound. The cover 106 may be placed over the manifold 120 and the bioresorbable component 130 and the cover 106 sealed to an attachment surface near the tissue site. For example, the cover 106 may be sealed to undamaged epidermis peripheral to a tissue site. In some other embodiments, the dressing 102 may be preassembled, for example, such that the bioresorbable component 130, manifold 120, and cover 106 are positioned with respect to each other prior to placement proximate the tissue site or, alternatively, the various components of the dressing 102 may be positioned with respect to the tissue site sequentially. Thus, the dressing 102 can provide a sealed therapeutic environment, for example, a sealed space like sealed space 107, proximate to a tissue site, substantially isolated from the external environment.

The negative-pressure source 104 may be used to reduce the pressure in such sealed therapeutic environment. For example, negative pressure applied across the tissue site, for example, via the dressing 102 can induce macrostrain and microstrain in the tissue site, as well as remove exudates and other fluids from the tissue site, which can be collected in container 112.

Advantages

In some embodiments, the dressings, the various combinations of dressing components, and systems may be advantageously employed in the context of negative-pressure therapy, for example, to provide a dressing exhibiting extended wear-time. For example, the bioresorbable component of the dressing may be adapted to be resorbed after a predetermined duration, for example, in the range of from several days to a few weeks. In some embodiments, the bioresorbability characteristics of the bioresorbable component allow the dressing to be left in place at the recipient site for substantial periods of time. For example, and not intending to be bound by theory, because the bioresorbable component of the dressing may be bioresorbable, the dressing does not necessitate removal, for example, to avoid in-growth of tissue (e.g., to ensure that the growing tissue at the recipient site does not become attached to the bioresorbable component). The capability to leave the dressing in place for longer periods of time can yield several advantages. For instance, by leaving the dressing in place, premature removal, potentially resulting in disturbance of or trauma to the tissue growth, may be avoided. Also, by leaving the dressing in place, trauma to the tissue site that would otherwise result from removal can be avoided. Additionally, leaving the dressing in place for sustained time periods may yield improved tissue growth.

Additionally, in some embodiments, the extended wear-time may allow the bioresorbable component to exhibit activity, such as protease-modulating activity, over the extended duration. For example, in operation, the degradation-modulating component may be effective to modulate (e.g., slow) the rate at which the bioresorbable component is resorbed and, thus, allow the bioresorbable component to exhibit activity, such as protease-modulating activity, over the extended duration. Further still, in some embodiments where the dressing comprises multiple bioresorbable components, the degradation-modulating component may be configured such that the various bioresorbable components (e.g., layers) may be resorbed at different, sequential intervals. For example, a first degradation-modulating component may be configured to modulate degradation of a first bioresorbable component such that the first bioresorbable component may be resorbed within a first time interval and a second degradation-modulating component may be configured to modulate degradation of a second bioresorbable component such that the second bioresorbable component may be resorbed within a second time interval. As such, and not intending to be bound by theory, by configuring the various bioresorbable components such that the various bioresorbable components provide activity (e.g., protease-modulating activity) over differing intervals, the dressing, cumulatively, may provide activity (e.g., protease-modulating activity) over an extended duration.

The term "about," as used herein, is intended to refer to deviations in a numerical quantity that may result from various circumstances, for example, through measuring or handling procedures in the real world; through inadvertent error in such procedures; through differences in the manufacture, source, or purity of compositions or reagents; from computational or rounding procedures; and the like. Typically, the term "about" refers to deviations that are greater or lesser than a stated value or range of values by ¹/₁₀ of the stated value(s), e.g., ±10%. For instance, a concentration value of "about 30%" refers to a concentration between 27% and 33%. Each value or range of values preceded by the term "about" is also intended to encompass the embodiment of the stated absolute value or range of values. Whether or not modified by the term "about," quantitative values recited in the claims include equivalents to the recited values, for example, deviations from the numerical quantity, but would be recognized as equivalent by a person skilled in the art.

The appended claims set forth novel and inventive aspects of the subject matter disclosed and described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described herein may also be combined or replaced by alternative features serving the same, equivalent, or similar purpose without departing from the scope of the invention defined by the appended claims.

What is claimed is:

1. A negative pressure system for providing negative pressure therapy to a tissue site, the system comprising:
    a manifold;
    a bioresorbable component having a first surface and a second surface opposite the first surface;
    a degradation-modulating component covering the first surface and the second surface of the bioresorbable component and configured to modulate degradation of the bioresorbable component, the degradation-modulating component comprising a polymer having a monomeric unit, the monomeric unit comprising vinyl pyrrolidone, vinyl alcohol, ethylene oxide, propylene oxide, ethylene glycol, acrylic acid, a salt of acrylic acid, an ester of acrylic acid, acrylamido methylpropane sulphonic acid, a salt of acrylamido methylpropane sulphonic acid, an ester of acrylamido methylpropane sulphonic acid, cellulose derivatives, copolymers thereof, blends or mixtures thereof, or combinations thereof,
    a cover configured to be placed over the manifold, the bioresorbable component, and the degradation-modulating component; and
    a negative-pressure source configured to be fluidly coupled to the manifold.

2. The negative pressure system of claim 1, wherein the manifold comprises a hydrophobic, open-cell foam.

3. The negative pressure system of claim 1, wherein the manifold is formed from polyurethane.

4. The negative pressure system of claim 1, wherein the bioresorbable component exhibits protease-modulating activity.

5. The negative pressure system of claim 1, wherein of the bioresorbable component comprises collagen and oxidized, regenerated cellulose.

\* \* \* \* \*